(12) United States Patent
Friesner et al.

(10) Patent No.: US 8,160,820 B2
(45) Date of Patent: Apr. 17, 2012

(54) BINDING AFFINITY SCORING FUNCTION INCLUDING FACTOR FOR ENVIRONS OF RING OR BULKY RIGID GROUP

(75) Inventors: Richard A. Friesner, New York, NY (US); Robert Murphy, Englewood Cliffs, NJ (US)

(73) Assignee: Shrodinger, LLC, New York, NY (US)

( * ) Notice: Subject to any disclaimer, the term of this patent is extended or adjusted under 35 U.S.C. 154(b) by 875 days.

(21) Appl. No.: 12/152,067

(22) Filed: May 12, 2008

(65) Prior Publication Data

US 2008/0312894 A1    Dec. 18, 2008

Related U.S. Application Data

(60) Provisional application No. 60/930,089, filed on May 14, 2007.

(51) Int. Cl.
*G06F 19/10* (2011.01)
(52) U.S. Cl. .......................................................... 702/22
(58) Field of Classification Search .................. None
See application file for complete search history.

(56) References Cited

U.S. PATENT DOCUMENTS

| | | | |
|---|---|---|---|
| 6,741,937 B2 * | 5/2004 | Waldman et al. ............... 702/23 |
| 2004/0171062 A1 * | 9/2004 | Hirth et al. ...................... 435/7.1 |
| 2005/0119837 A1 * | 6/2005 | Prakash et al. .................. 702/27 |
| 2005/0228592 A1 * | 10/2005 | Ahuja et al. ..................... 702/19 |
| 2007/0061118 A1 | 3/2007 | Friesner et al. |
| 2007/0066641 A1 * | 3/2007 | Ibrahim et al. ................. 514/300 |
| 2010/0112724 A1 * | 5/2010 | Tovbin et al. ................... 436/501 |

FOREIGN PATENT DOCUMENTS

WO    WO 2006/099178    9/2006

OTHER PUBLICATIONS

Freisner et al. J. Med. Chem. (2004) vol. 47, pp. 1739-1749.*
Stahl et al. J. Med. Chem. (2001) vol. 44, pp. 1035-1042.*
Sherman et al. J. Med. Chem. (2006) vol. 49, pp. 534-553.*
Eldridge et al. J. Comput. Aid. Mol. Des. (1997) vol. 11, pp. 425-445.*
Friesner et al. J. Med. Chem. (2006) vol. 49, pp. 6177-6196.*
Zhou et al. J. Chem. Inf. Model. (2007) vol. 47, pp. 1599-1608.*

* cited by examiner

*Primary Examiner* — Lori A Clow
(74) *Attorney, Agent, or Firm* — Fish & Richardson P.C.

(57) ABSTRACT

Scoring functions can be markedly improved by taking into account the status environs of ligand rings (or indeed other bulky rigid ligand structures) on the ligand when the ligand is complexed with the receptor. In its most general form, the invention features, quantifying a particular component of binding affinity between a ligand and a receptor molecule. Specifically, the component in question takes into account the spatial relationship between ligand ring structure(s) (or bulky rigid ligand structures) and their ambient surroundings when the ligand is bound to the receptor molecule. The method steps may be used when quantifying a component that reflects these particular ligand features alone, or the steps may be part of a comprehensive method of quantifying binding affinity which includes numerous other factors that relate to binding affinity in addition to the component. For example, one may calculate an initial binding affinity and then adjust the initial binding affinity by a factor obtained at least in part based on the classification of the ring structure.

21 Claims, 10 Drawing Sheets

(3 of 10 Drawing Sheet(s) Filed in Color)

FIG. 1 (CDK2- 1aq1)

FIG. 2 (1d3d)

BINDING AFFINITY SCORING FUNCTION INCLUDING FACTOR FOR ENVIRONS OF RING OR BULKY RIGID GROUP

CROSS-REFERENCE TO RELATED APPLICATIONS

This application claims priority to U.S. Application Ser. No. 60/930,089, filed on May 14, 2007.

TECHNICAL FIELD

The invention is in the general field of computer-based methods for estimating binding affinity between a ligand and a receptor molecule.

BACKGROUND

Many drugs operate by chemically binding to specific molecular receptors. Molecular receptors typically are specific proteins (a term that includes glycoproteins and lipoproteins) in an animal such as a human being, and drug design and selection can be facilitated by accurately estimating the binding affinity of a drug to a protein, or, more generally, estimating the binding affinity of a ligand to a receptor, the term receptor being used to mean any moiety that specifically binds the ligand.

One way to determine receptor-ligand binding affinity uses the molecular structure of the receptor-ligand complex that results when the ligand binds to the receptor. Such structures may be studied by x-ray crystallography. The publicly accessible protein data bank (PDB) now contains more than 10,000 x-ray crystal structures, and pharmaceutical and biotechnology companies have an order of magnitude more proprietary structures. Many of these structures have been co-crystallized with small molecules bound to them. The examination of such structures, and deployment of the knowledge thereby gained to design new, more potent, and more specific inhibitors, is referred to as structure-based drug design.

Computational modeling facilitates structure-based drug design. One aspect of modeling detailed below involves scoring functions that use simulation techniques, such as molecular dynamics, Monte Carlo, or continuum electrostatics calculations. These scoring functions can be problematic, as one is required to calculate a very small difference (the binding affinity) between two very large numbers (the free energies of the complex and of the separated protein and ligand). An alternative approach is to develop an empirical scoring function, based on the geometry of the complex, which directly evaluates the desired quantity. Such an approach has the advantage of being extremely fast as well as being amenable to fitting to experimental data, large amounts of which are now publicly available. Our own application, U.S. patent application Ser. No. 11/373,684 (US 2007/061118) entitled "Predictive Scoring Function for Estimating Binding Affinity," which is hereby incorporated by reference in its entirety, discloses scoring functions.

It is desirable to increase the accuracy and robustness of scoring functions. It is particularly desirable to use scoring functions not only to distinguish active from inactive ligands, but also to rank ligands in a group of ligands, e.g., from most active to least active, to identify more promising candidates to be studied ahead of less promising candidates. Moreover, the ability to rank order a group of ligands having different chemotypes would allow one to search a broader range of candidates for effective drugs. Finally, rank ordering ligands without a large amount of preliminary work (e.g., using a training set) would further increase the convenience and speed of the process.

SUMMARY

We have discovered that scoring functions can be markedly improved by taking into account the environs of ligand rings (or indeed other bulky rigid ligand structures) when the ligand is complexed with the receptor. In its most general form, the invention features quantifying a particular component of binding affinity between a ligand and a receptor molecule which takes into account the spatial relationship between ligand ring structure(s) (or bulky rigid ligand structures) and their ambient surroundings, when the ligand is bound to the receptor molecule. The method steps we have developed may be used when quantifying a component that reflects these particular ligand features (e.g. ligand rings) alone, or the steps may be part of a comprehensive method of quantifying binding affinity which includes numerous other factors that relate to binding affinity in addition to the component reflecting rings or bulky rigid structures. For example, one may calculate an initial binding affinity and then adjust the initial binding affinity by a factor obtained at least in part based on the classification of the ring structure.

In one aspect, the invention generally features: a) identifying a ring structure within the ligand; classifying the ring structure based on the spatial relationship of the ring structure to its ambient surroundings when the ligand is bound to the receptor molecule; quantifying at least the component of the binding affinity between the ligand or part thereof and the receptor molecule based at least in part on the classification of the ring structure; and displaying, via computer, information related to the classification of the ring structure. In this context, we use the term "ring structure" to mean either an entire ring, a set of fused rings or a portion of a ring or of a fused ring. Preferably the ring structure includes a complete ring, or it consists of connected atoms which make up a portion of a ring or of a fused ring. For example the ring structure may be classified according to the spacial relationship between the ring structure and the receptor, based on how exposed the ring structure is to surrounding solvent.

In preferred embodiments of this aspect of the invention, the ring structure is assigned one of the following classifications: a) buried; b) solvent exposed; or c) solvent exposed on one surface, although additional classifications or subclassifications may also be used. Also preferably, the method includes a step that scores hydrophobic interactions between one or more ligand atoms and one or more receptor atoms by awarding a bonus for the presence of hydrophobic enclosure of one or more ligand atoms by the receptor molecule. The bonus is indicative of enhanced binding affinity between the ligand and the receptor molecule. To classify the ring structure one may obtain a value representative of the spatial relationship between the ring structure and its ambient surroundings when bound to the receptor molecule by a) classifying a ring structure as buried if the value is above a first amount; b) classifying a ring structure as solvent exposed if the value is below a second amount, and c) classifying a ring structure as having a single face exposed to solvent if the value is an amount between the first and second amount. In one embodiment: a) the number of close contacts at different distances between receptor atoms and the two ring faces are determined, b) an initial classification of the ring is made based on the numbers of these contacts, and c) this initial classification is followed by calculation of a scoring function, dependent upon other parameters, which enables the final classification as buried, solvent exposed, or solvent exposed on one surface. The number of close contacts at different distances between receptor atoms and the two ring faces may be determined in order to make an initial classification of the ring based on the numbers of these contacts, and this initial classification is then followed by calculation of a scoring function, dependent upon other parameters which enable the final classification as buried, solvent exposed, or solvent exposed on one surface.

Preferably, the scoring function enabling classification of the ring structure includes calculating the degree of enclosure of each atom of the ring structure by atoms of the receptor. It may also include using a parameter that is substantially correlated with the degree of enclosure of each atom of the ring structure by atoms of the receptor. Where the ambient surroundings of the ring structure when bound to the receptor molecule include water molecules, the scoring function may include the use of a parameter corresponding to a number of water molecules in a first shell of the ring structure, or in a second shell of the ring structure or in a combination of the first shell and the second shell. The scoring function enabling classification of the ring structure as buried, solvent exposed, or solvent exposed on one surface may also include the use of a parameter substantially correlated with the number of close contacts on both sides of the ring structure or part thereof with the receptor molecule. It may also include use of a parameter corresponding to a hydrophobic interaction of the ring structure or part thereof with the receptor molecule. Finally, it may include use of a parameter substantially correlated with the lipophilic-lipophilic pair score between the ring structure or part thereof and the receptor molecule.

Where the ring structure includes fused rings, the quantification method includes at least one step accounting for ring fusion. For example, accounting for ring fusion results in a binding affinity that is lower than the affinity obtained without such accounting, by an amount related to the degree of ring fusion.

Specific steps in the quantification and in the ring structure classification scoring function are found in the Appendix to this application. These steps may be used individually or in combination. Alternatively, one may obtain a preliminary binding affinity and adjust that preliminary binding affinity based on a display of the ring structures.

When a ring structure is designated solvent exposed it is substantially ignored in quantifying the binding affinity component, other than to recognize hydrogen bonds and other parameters that are independent of the classification of ring structure. More specifically, the hydrophobic contribution from solvent exposed ring structures to the binding affinity is substantially ignored in quantifying the component of the binding affinity, but other aspects of solvent exposed rings (e.g., hydrogen bonds) may be recognized.

The above method may include methods that identify strain energy induced in the ligand when bound to the receptor molecule and to use that strain energy quantity when quantify the binding affinity component. For example, the method may include: a) identifying a quantity representative of a strain energy induced in the ligand-receptor complex by the aggregate of the ring structures identified as buried; b) identifying a quantity representative of a total neutral-neutral hydrogen bond energy; and c) quantifying the component of binding affinity between the ligand and the receptor molecule based at least in part on the quantity representative of the strain energy induced in the receptor by the aggregate of the buried ring structures, and on the quantity representative of the total neutral-neutral hydrogen bond energy. In addition, the binding affinity may include identifying a hydrogen bond capping energy associated with the entire ligand, in which case binding affinity component is quantified based on a greater of the hydrogen bond capping energy and the quantity representative of the strain energy induced in the receptor by the aggregate of the identified structures. The binding affinity component attributable to strain may be quantified using: molecular dynamics, molecule mechanics, conformational searching and/or minimization.

The information displayed by computer may include a depiction of solvent exposure, if any, of the ring structure. It may also include a depiction of burial, if any of ring structure(s). Other information displayed includes a depiction of at least one of the following: a) the degree to which the ring structure is enclosed by atoms of the receptor molecule; b) water molecules surrounding the ring structure in a first shell or a second shell or both the first and the second shell of the ligand; c) a value of a lipophilic-lipophilic pair score of the ring structure; and number of close contacts of a face of the ring structure with the receptor molecule.

The method may include identifying a binding motif of the receptor molecule with respect to the ligand, and quantifying the binding affinity based on the binding motif. A reorganization energy of the receptor may be identified based on the binding motif. More specifically the method may include: a) identifying a binding motif of the receptor molecule with respect to the ligand; b) identifying a reorganization energy of the receptor molecule based on the binding motif; and c) identifying a first ring structure as contributing to the reorganization energy. The quantity representative of strain energy is identified independently of the classification of the first ring structure.

Having performed the quantification described above, one may then perform a test on a physical sample that includes the ligand and the receptor molecule, and one may select test components based at least in part on the binding affinity between the ligand or part thereof and the receptor molecule, or on the component of such binding affinity. For example the test may be used to measure a therapeutic efficacy of the receptor in the treatment of a malady.

A more generally stated invention features the above-described method of quantifying a component of binding affinity, in which the ligand structure identified is a bulky rigid structure within the ligand, rather than a ligand ring structure. Such bulky, rigid structure include: a) t-butyl group; b) structures that include four connected heavy atoms; c) group of atoms connected by rigid torsional bond angles having a freedom of movement less than 5-10 degrees.

Other features and advantages of the invention will be apparent from the description of the drawings, the detailed description and from the claims.

DESCRIPTION OF DRAWINGS

The file of this patent application contains at least one drawing executed in color. Copies of this patent with color drawings will be provided by the Patent and Trademark Office upon request and payment of the necessary fee.

DETAILED DESCRIPTION

Figure 1:
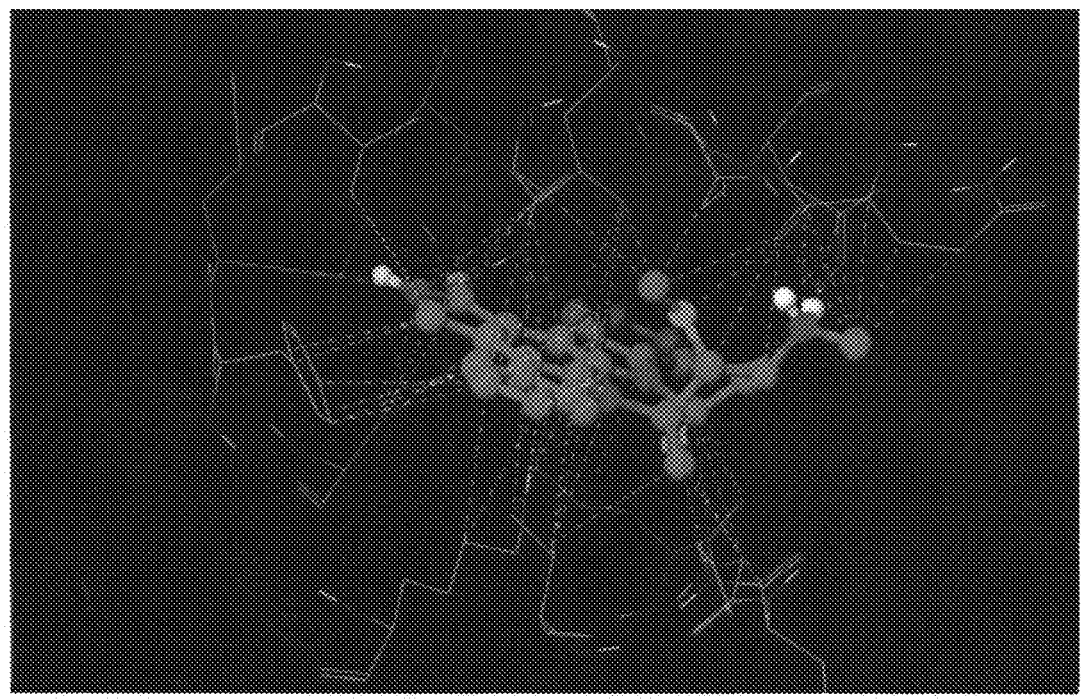
FIG. 1 is a depiction of the protein-ligand complex 1aq1 from the protein data base (PDB). The Figure shows the enclosure of the various subrings in the large 1aq1 fused ring system by the protein, many of which are defined as buried by the current best practice classification scheme; it also shows the hydrogen bonds between the ligand and protein.

Given a high resolution receptor structure (with the receptor typically a protein), computational software is used to "dock" a small molecule ligand into the correct position and orient it in the receptor active site cavity, and calculate a binding affinity of the ligand given this structure. Computer software programs that perform this task are referred to as "docking" programs.

A docking program typically carries out two distinct tasks to model receptor-ligand binding. First, a structure of a receptor-ligand complex is predicted. When this assumption fails, use of a different structure of the receptor as a starting point is required. The problem of constructing alternative receptor structures that are modified to accept ligands requiring a substantial change in receptor conformation ("induced fit") is a very important one.

We focus here on cases where docking of the ligand into a receptor yields a structure in reasonable agreement with experimental data, and particularly we focus on a second task of the docking program, which is to calculate a receptor-ligand binding affinity, given as an input the docked structure. A mathematical function employed to calculate the binding affinity (or a contribution thereto) is referred to as a "scoring function."

The estimates of receptor-ligand binding affinities described below are applicable when a structure of the receptor-ligand complex is represented by a suitable structural model. There are a number of ways to characterize the quality of structural models of receptor-ligand complexes. To obtain accurate scores, one generally needs a small root mean square deviation (RMSD) from the experimental structure (typically less than 2 Angstroms, although the required value will vary depending upon details of the complex), formation of substantially all hydrogen bonds seen in the experimental complex, appropriate placement of substantially all hydrophobic groups in the correct receptor cavities, and the absence of incorrect structural or electrostatic clashes that could lead to the assignment of substantially incorrect penalty terms. Only relative binding affinity of ligands to a given receptor matters; a constant offset, as is in many cases engendered by reorganization energy of the receptor active site to accommodate the ligand, has no effect on practical applications. In many (although not all) cases, the receptor can adopt more than one fundamentally different conformation in response to a class of ligands (e.g., DFG-in and DFG-out binders to p38 map kinase); to compare the binding free energies in such cases, different core reorganization parameters may be required for the different receptor conformations. Where calculation of these parameters is not practical from first principles they are treated as adjustable, receptor specific parameters. Other parameters are however contained in a global model which is not receptor-specific or even specific to a particular class of receptors.

In the present application, we focus on calculation of important components of the ligand binding affinity when an adequately accurate structure for the ligand-receptor complex, as defined above, is available. The method is operable for ligands for which there are crystal structures are not available. However, as a control for evaluating the method, the examples below involve known crystal structures available in the Research Collaborative for Structural Bioinformatics' publicly accessible Protein Data Bank ("the PDB"). In carrying out optimization, we use poses docked with Glide XP, a scoring function described e.g., in U.S. patent application Ser. No. 11/373,684, entitled "Predictive Scoring Function for Estimating Binding Affinity," filtering the (very small) number of cases for which self-docking yields unsuitable structures. By using docked structures, rather than the crystal structures themselves, in our optimization process, we increase the realism of the model, and also enable the docking to correct small geometrical errors in the crystal structures (eg in hydrogen bond distances) which can be crucial to properly assigning scores to these terms. The invention does not require the use of ligands for which crystal structures are known, nor does it require the use of Glide XP.

The PDB structures can be viewed as a large and diverse training set for the scoring function. Testing of the scoring function under similar conditions can be performed by pharmaceutical and biotechnology companies, using proprietary data sets where crystal structures are available. In carrying out these tests, there is no need to release the structures or even to divulge the name of the receptor; one can simply perform the calculations, and report the ability to rank order the compounds as a correlation coefficient.

The qualitative behavior of pharmaceutical compounds interacting with protein receptors is, in many cases, dominated by the interaction of bulky, rigid groups on the ligand with the receptor. A group is "bulky" if it includes four or more heavy (e.g., non-hydrogen) atoms. A group is "rigid" its constituent bonds possess less than a pre-determined threshold of torsional freedom. In some implementations, the threshold is between 5 and 10 degrees. For example, bulky, rigid structures include rings and tert-butyl groups.

By far the most important bulky, rigid structures are ring structures. Types of ring structures include aromatic and saturated rings, fused rings, and a connected subset of atoms in a single ring or fused ring. In what follows, we shall focus primarily on an algorithm for improving the characterization of the binding affinity contribution made by ring structures to the total ligand binding affinity. The algorithm may also apply to other bulky rigid structures, however, a detailed model for structures other than ring structures has not yet been developed.

Binding affinity is typically influenced by the interaction of ring structures of the ligand with primarily hydrophobic cavities of the receptor. For example, U.S. patent application Ser. No. 11/373,684 (US 2007/061118), referred to above, identified situations where particularly large increments of binding affinity can be obtained, namely, when a ring is subject to hydrophobic enclosure by the protein, and when the ring is complementary to any polar groups in the enclosed region (i.e., forming hydrogen bonds as necessary, but presenting no other polar or charged groups to the hydrophobically enclosed cavity).

We have investigated other aspects of how ring interact with the receptor. This more general examination has led to the development of the improved methods for calculating components of the binding affinity disclosed herein. These components have a physical basis that can be readily described, and is subject to investigation via atomistic simulations. The components can be used in and of themselves to better understand the effect on binding affinity of adding to or removing from a ligand specific ring structures. They can also be used, in combination with other scoring function components, to produce a combined scoring function which yields a better representation of binding affinity than was available in previous work. Specifically, in combination with the Glide XP scoring function described in U.S. patent application Ser. No. 11/373,684 (US 2007/061118), a scoring function can be developed that enables semiquantitative rank ordering of ligands with respect to binding affinity to the receptor. Examples of such rank ordering are discussed below.

In what follows, we begin with a classification of ring structures of the ligand into three classes, depending upon the nature of their spatial interaction with the receptor. We then develop quantitative measures for assigning any given ring structure into one of the three classes, using a variety of descriptors. Finally, the deployment of the classification scheme in the scoring function is presented, including specific formulas for computing binding free energy components on a per-ring-structure basis, and assembly of these terms into a component of the binding affinity for the entire ligand.

Ring Classification Scheme

Figure 2:
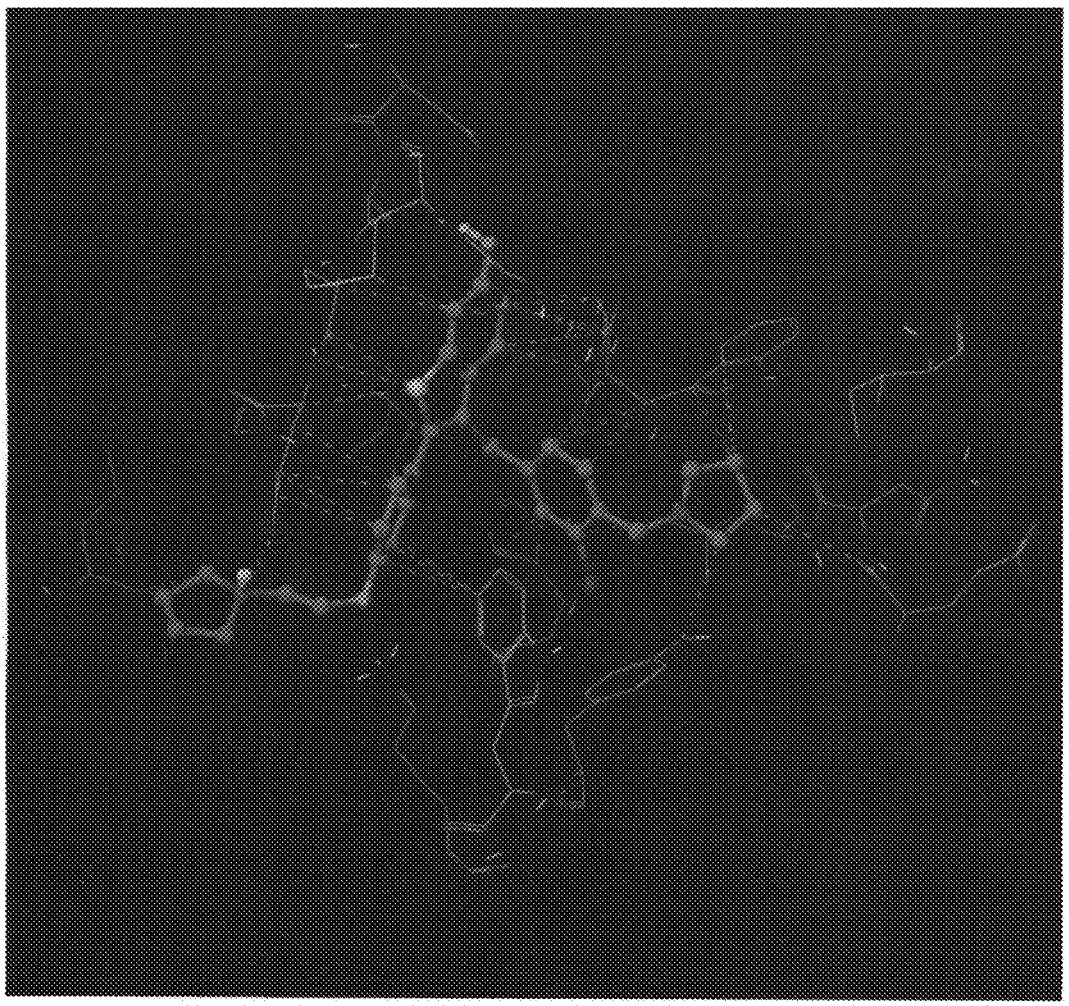
FIG. 2 is a depiction of the protein-ligand complex 1d3d from the PDB. The Figure shows the enclosure of the various rings of the 1d3d ligand by the protein, which are defined as buried by the current best practice classification scheme. Note that there are very few hydrogen bonds in the structure.

We classify ring structures into one of the following three categories:

(1) Buried ring structures. These are structures that are inserted into a receptor cavity, with receptor atoms proximate to both faces of the ring, and predominantly isolated from aqueous solvent. The classification of a ring structure as buried is achieved by a scoring function dependent upon quantitative descriptors measuring enclosure, number of solvent molecules proximate to the ligand, number of close contacts on both faces of the ligand, and hydrophobic interactions with the receptor, as described in more detail below. FIGS. 1 and 2 display structures from the PDB which contain a significant number of buried ring structures.

(2) Surface ring structures. These are structures for which the primary contact with the receptor is made by only one face of the ring structure, with the other face predominantly exposed to solvent. The question of the boundary between an buried structure and a surface structure—that is, how much contact with the protein does the second face have to have in order to be placed into category (1) above, as opposed to category (2)—is a quantitative one, and requires discrimination using the numerical scoring function discussed above.

Figure 3:
FIG. 3 is a depiction of the protein-ligand complex 2d3u. The ligand contains two rings (those on the right hand side of the Figure) which are defined as solvent exposed by the current best practice classification scheme. A buried ring is shown on the left hand side of the ligand.
Figure 4:
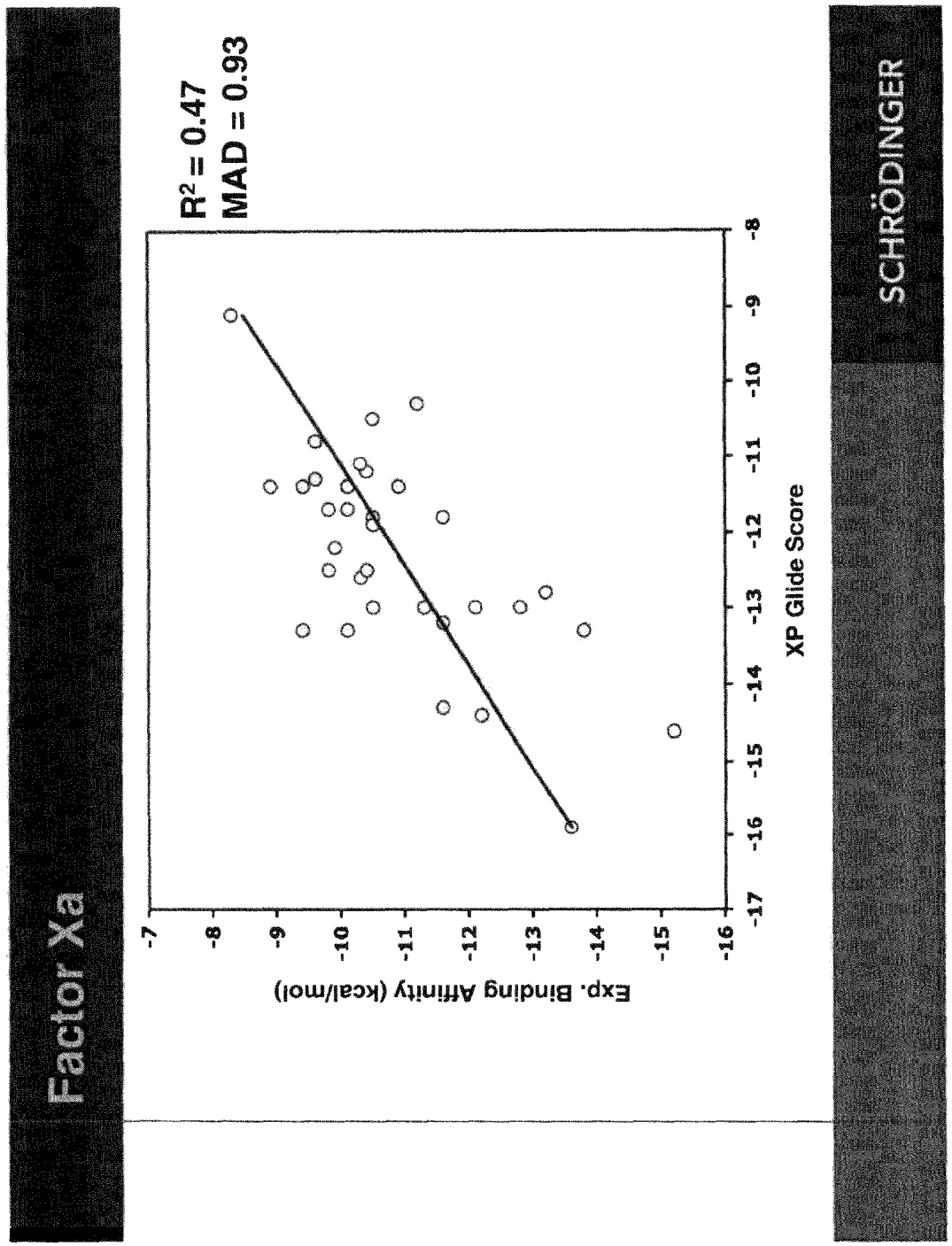
FIGS. 4-10 represent results obtained with the current best practice implementation of the invention for protein-ligand complexes in the PDB for 7 different receptors, comparing calculated binding affinities with experimental binding affinity data. The results obtained in FIGS. 4-10 are discussed in more depth in the Detailed Description below.
Figure 5:
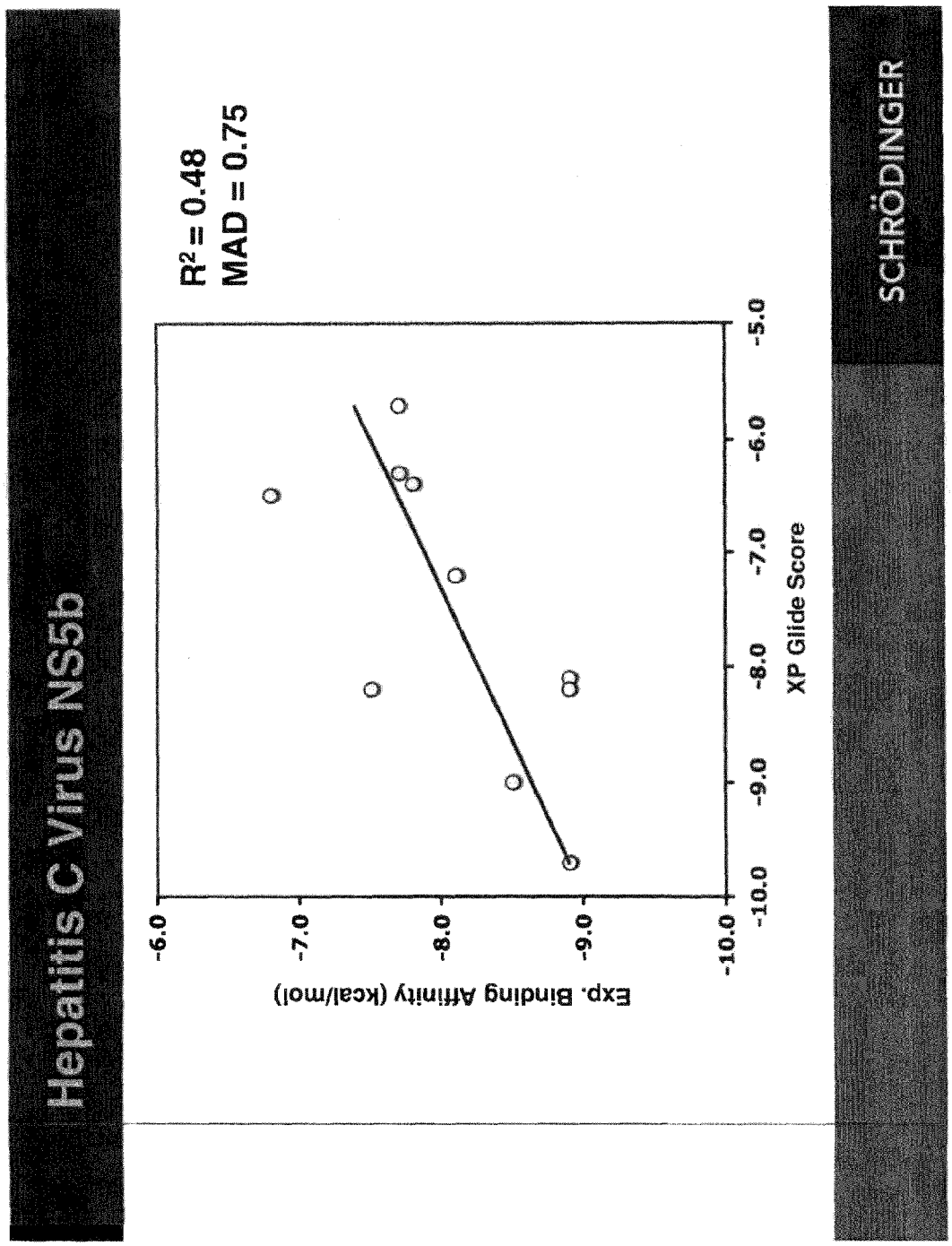
Figure 6:
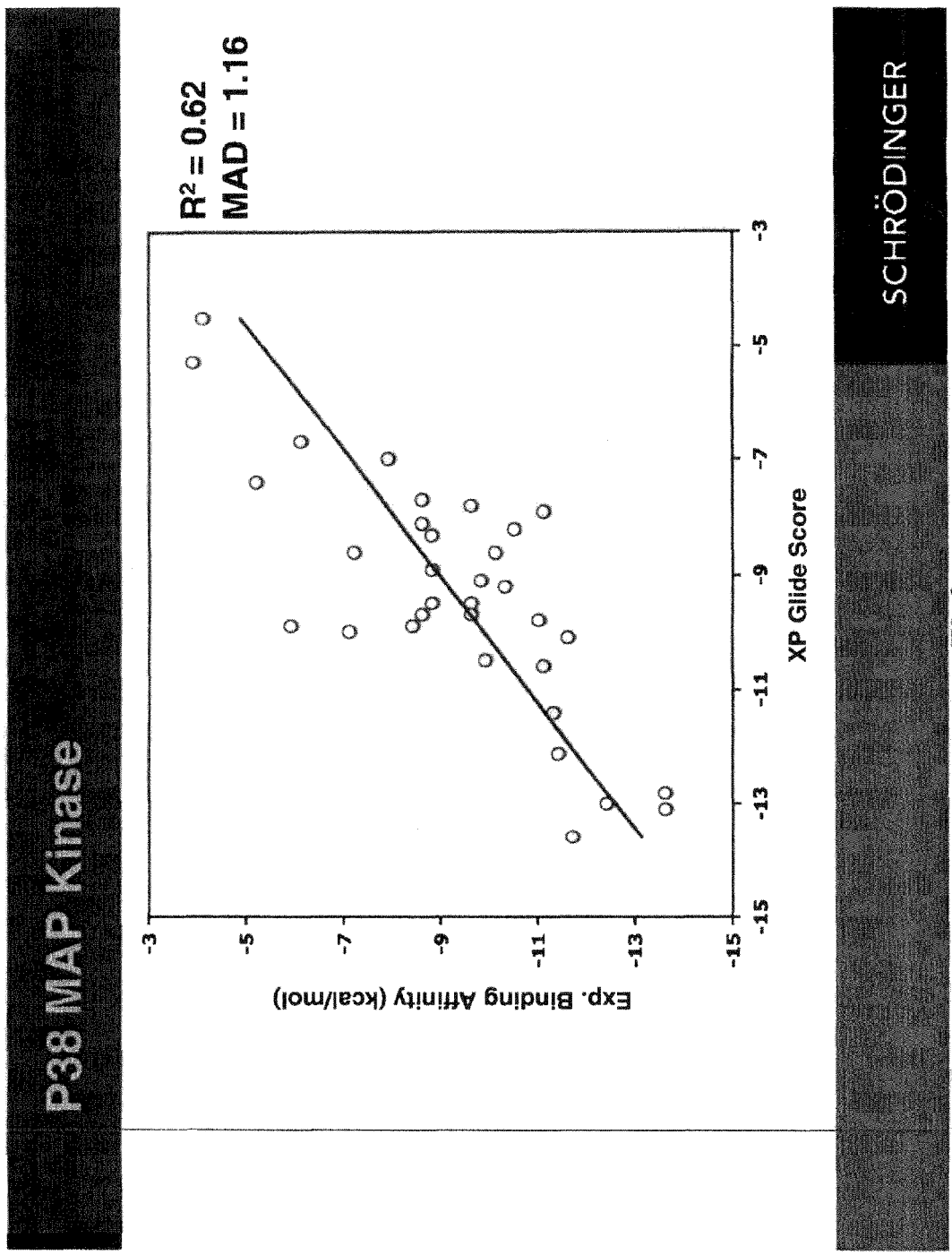
Figure 7:
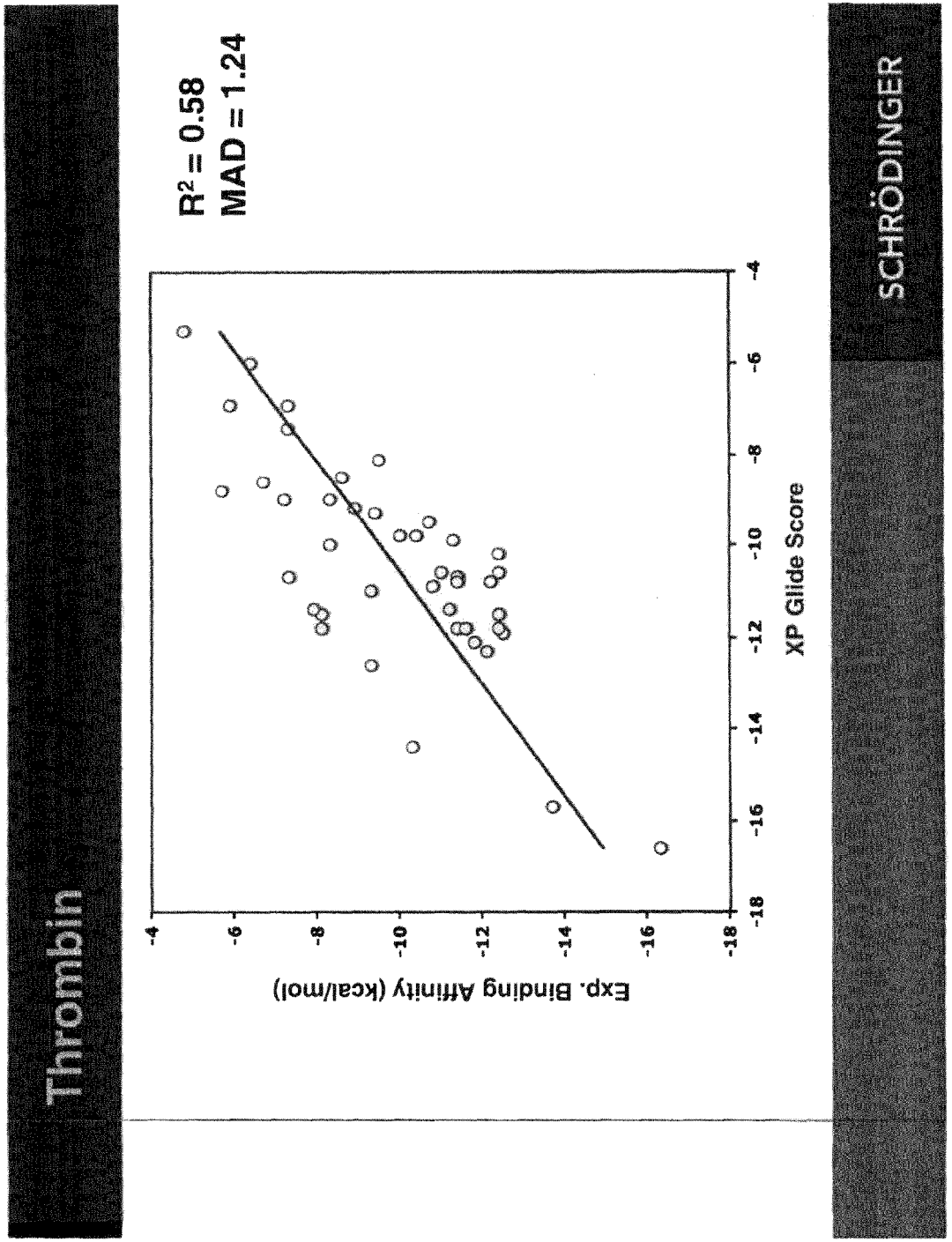
Figure 8:
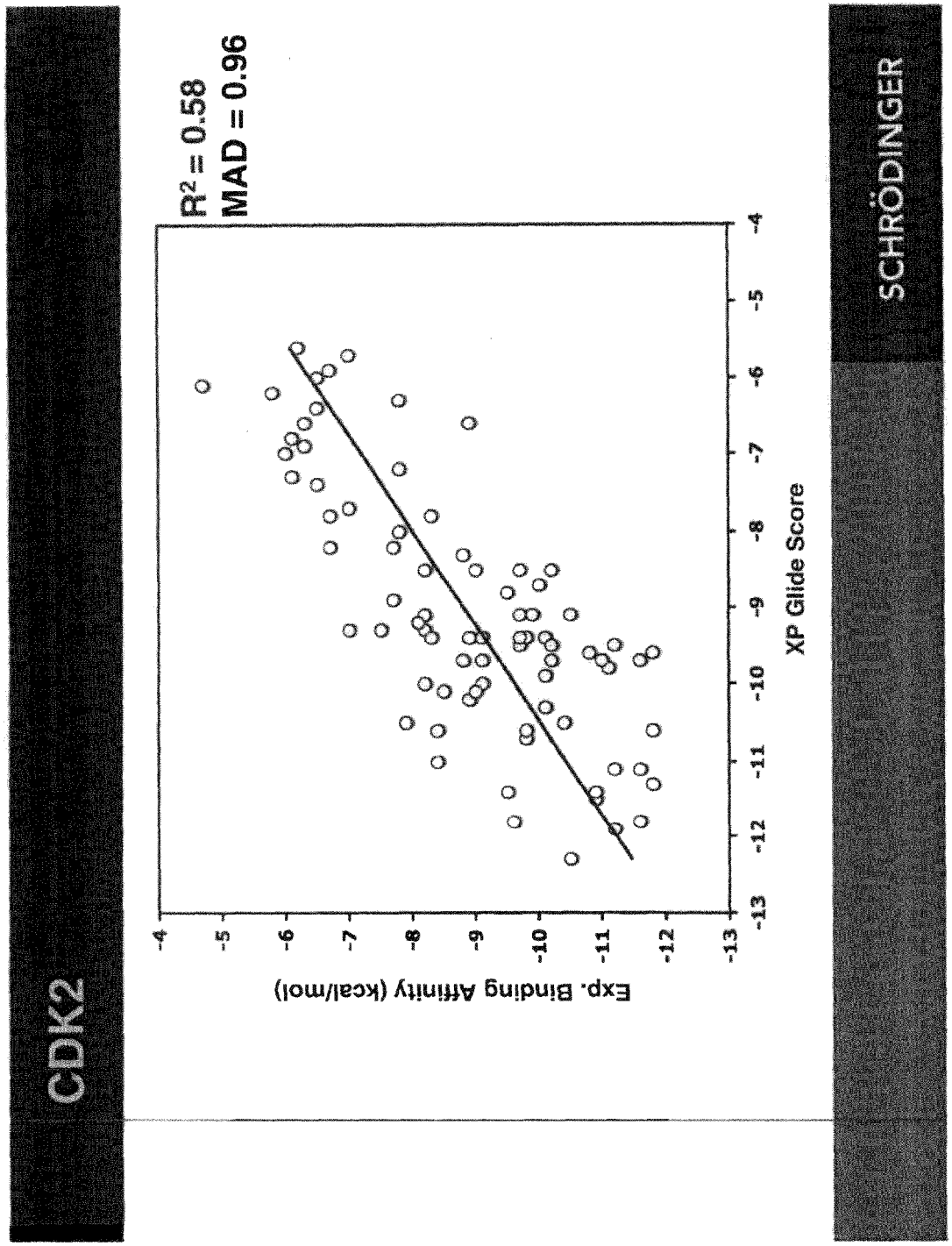
Figure 9:
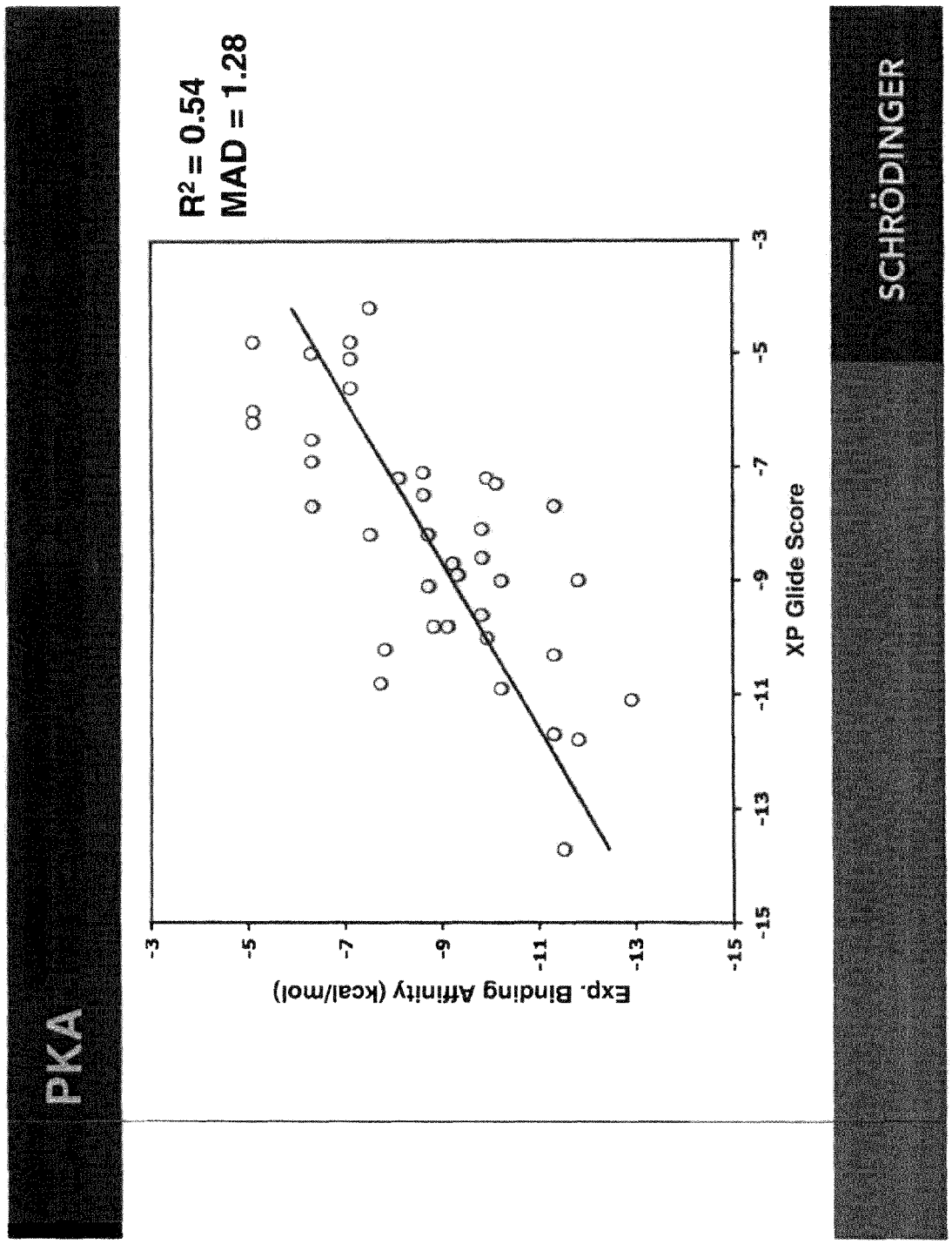
Figure 10:
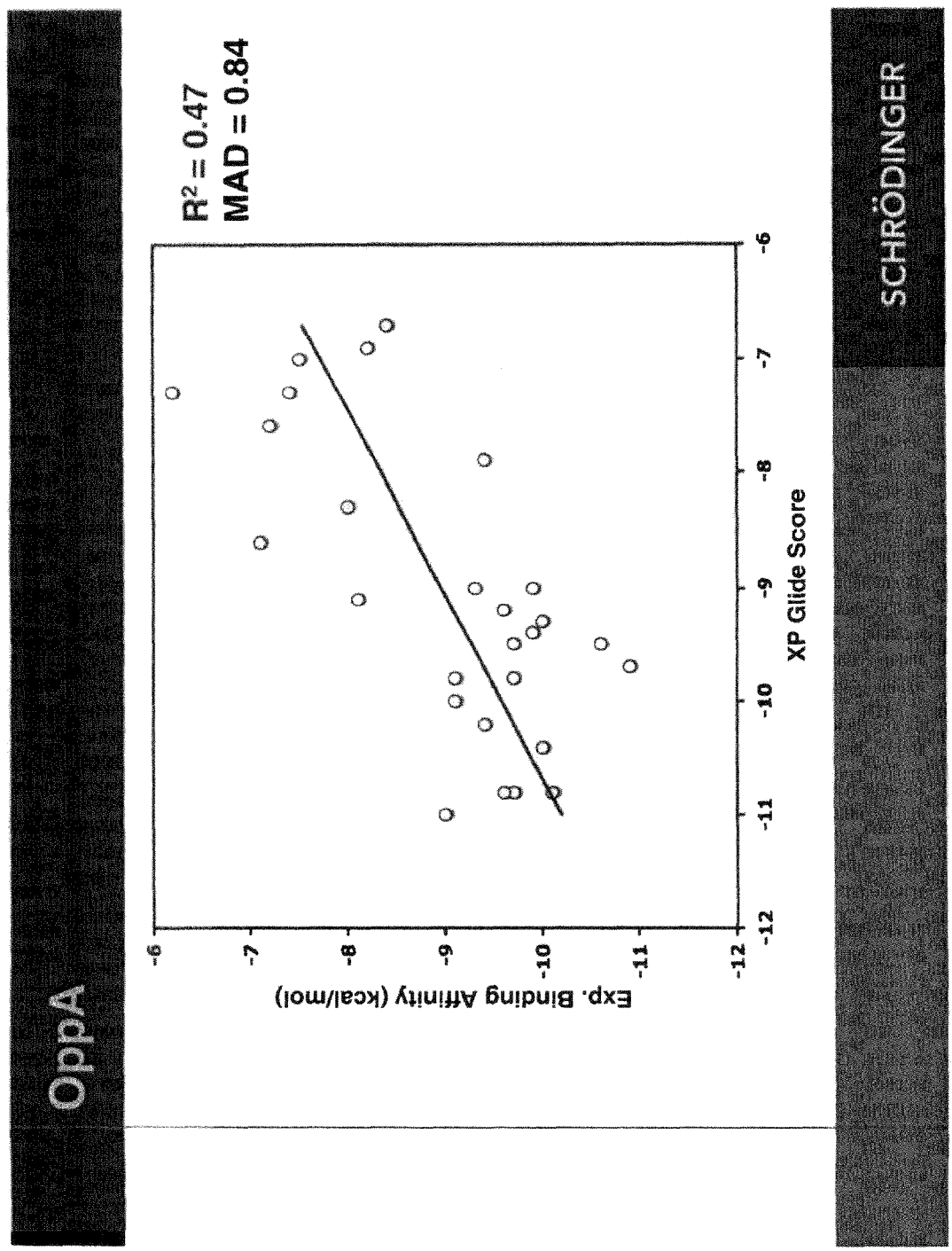

(3) Solvent exposed structures. These are structures for which both faces of the ring structure are primarily in contact with solvent, as opposed to the protein. Again, quantitative criteria must be designed to separate solvent exposed ring structures from surface ring structures, based on the same numerical scoring scheme as discussed above. One might ask why any ring structures are solvent exposed, as opposed to making the best contact available with the receptor with one face of the structure. Sometimes such contact is geometrically infeasible; in other cases, the part of the surface that could be contacted is unsuitable, possessing polar or charged groups that would be desolvated were the ring structure to approach the receptor closely. FIG. 3 displays a complex from the PDB containing two solvent exposed rings and one buried ring.

Having defined the three classes of ring structures above, we now discuss the numerical algorithms that are used to classify a given structure into one of the three above categories. In some implementations of classifying ring structures, including that used in our current best practice implementation, only the heavy atoms comprising the core of the structure are considered. One may also considering atoms directly attached to the heavy atoms. For fused structures (i.e., structures for which are comprised of two or more overlapping sub-structures), each sub-structure is assessed separately. This can entail double counting of some of the atoms shared between sub-structures. The double counting is (approximately) taken into account in the final scoring function, as described below.

The first step in classifying the structure is to produce descriptors associated with each atom in the structure. We employ three descriptors for each atom:

(1) A function measuring the enclosure of the atom by the receptor. We use for this purpose the mathematical function modeling hydrophobic enclosure described in the Appendix of U.S. patent application Ser. No. 11/373,684 (US 2007/061118), although with different parameters as described in the Appendix of the present application, principally to weight closer atoms more heavily. A second and major difference in the function used here is that all protein heavy atoms, rather than only lipophilic atoms, are used to compute the enclosure. This function directly assesses the degree of spatial enclosure of the atom in the ring structure by the receptor.

(2) The number of water molecules in the first two shells surrounding the atom. In simulated binding, waters are explicitly added to the protein-ligand complex and assignment of waters to shells is performed by defining the first shell as waters in direct contact (based on the van der Waals radius of the ligand atom and a water molecule) with the ligand atom in question, while the second shell is defined as water molecules in van der Waals contact with the first shell. This value provides a direct measure of the degree of solvent exposure of the atom.

(3) The lipophilic atom-atom pair term representing interactions of the ligand atom with the receptor lipophilic atoms. This function provides a measure of how close the atom is to lipophilic atoms on the protein surface (without discriminating the geometrical arrangement of the surrounding atoms).

The second step is to enumerate the number of close contacts with the receptor made by the two faces of the ring. A contact is "close" to a face if it is within 6 Å of an atom in the ring, and satisfies an angular criterion with respect to the ring plane defined in the Appendix. To make the assessment of how containing the close contacts are more accurate, we count the number of protein heavy atoms within various distance cutoffs (e.g., 4 Å, 4.5 Å, 5 Å) of each face of the structure. The details of how atoms are assigned to "count" for a given face of the structure are given in the Appendix.

These descriptors are then combined to effect the classification of the structures. The enclosure, water and lipophilic pair terms are summed over the atoms in the structure to obtain a single value of each term. Qualitatively, the use of the descriptors in the classification function is as one would expect. In order to be classified as solvent-exposed, a structure has a relatively large number of surrounding waters, a relatively small value of the enclosure term, and a relatively small number of close contacts. Surface structures have a relatively small value of the enclosure term, contacts predominantly on one side of the structure (but possibly many contacts on that side), and an intermediate number of surrounding waters. Enclosed rings will have a relatively large value of the enclosure term, a relatively small number of surrounding waters, and close contacts on both sides of the ring. Adding the lipophilic pair term to the enclosure term produces a smoothing effect which provides a somewhat better measure of how closely the structure interacts with the protein surface.

A detailed classification scheme is presented in the Appendix to this application. The scheme uses a partitioning approach which incorporates some nonlinear elements; the contact terms are grouped to form clusters, and then within each cluster, cutoff values, representing boundaries between buried, surface, and solvent exposed ring structures, for the "ring score" (lipophilic plus enclosure term) and number of surrounding waters are defined. The cutoff values have been fit to reproduce the experimental data for the protein receptors presented below in FIGS. 4-10.

Binding Affinity Scoring Function

To convert the ring structure classification scheme into a scoring function which provides a component of the predicted binding affinity, we use a number of physical hypotheses concerning how each structure type interacts with the receptor.

We enumerate the key physical hypotheses as follows:

(1) A typical lipophilic atom-atom pair term, such as is used in the Glide XP, Glide SP, or GOLD scoring functions (described in detail in U.S. patent application Ser. No. 11/373, 684 (US 2007/061118), arising from solvent exposed structures overestimates the free energy gain associated with such structures. Since no face of the structure is shielded from water, nor is any of the receptor surface, via lipophilic contacts, there is no reason to believe that the overall free energy of the water molecules in the system have been made more negative (decreased). Such free-energy decrease is implicitly the source of the lipophilic atom-atom pair term. Favorable contributions to binding affinity from solvent exposed structures arise because the typical lipophilic atom-atom pair term has a relatively long "tail," extending 4-6 Angstroms from the ring atoms, which can capture substantial binding affinity score from receptor atoms that are not in van der Waals contact with the ligand. This score may make sense for surface or buried structures, but the results for solvent exposed structures are, based on our data, erroneous. A way to overcome this over-estimate is simply to eliminate the lipophilic atom-atom pair term (or other favorable hydrophobic contribution to binding affinity) for any ring structure classified as solvent exposed.

(2) Insertion of a structure into an enclosed pocket of the receptor can potentially induce strain energy in the receptor. In some cases, either receptor, or ligand, or both, has to adjust to optimize how the structure fits into the pocket. Bulky, rigid structures such as ring structures, can create strain when binding inside such a pocket, whereas other types of structures (e.g. a linear aliphatic hydrocarbon chain, which has a lot of flexibility to adjust torsional angles at a low energetic cost) can respond much more easily to confinement in the enclosed pocket.

(3) Empirically, we have found that only receptor-ligand complexes with a significant contribution to the binding free energy from neutral-neutral hydrogen bonds (hydrogen bonds between a net-neutral group on the ligand and a net-neutral group on the protein) appears to manifest induced strain energy from hypothesis (2). For example, complexes with little or no neutral-neutral hydrogen bond energy rarely, if ever, appear to manifest such strain energy, as estimated by the difference between a scoring function that does not include strain and the experimental binding affinity.

This observation, which links strain to neutral-neutral hydrogen bonding energetics has an intuitive physical basis. Unlike salt bridges or charge-neutral hydrogen bonds, neutral-neutral hydrogen bonds require precise geometries to achieve decent electrostatic interactions, due to the dipole-dipole nature of the electrostatics, which falls off rapidly as the distance and/or angular configuration becomes nonoptimal. Other scoring functions attempt to measure this falloff, but do not take into account situations where the receptor pays the energy cost by reorganizing to allow the hydrogen bond geometries to be optimally constructed. The presence of buried ring structures adds additional geometrical constraints. Satisfying these constraints at the same time as those required for strong neutral-neutral hydrogen bonds appears to impose difficulties on the complex that it can only escape from by expending free energy. The scoring function described below employs a simple empirical correction scheme, in which induced strain and neutral-neutral hydrogen bonding energy are interlinked.

We show below two examples of complexes from the PDB that contain a substantial number of buried ring structures. The first (FIG. 1) is the PDB complex 1aq1 which is a complex between a ligand (shown in the Figure) and the protein CDK2. In this complex there are a significant number of neutral-neutral hydrogen bonds including a "special pair" of hydrogen bonds that, in the Glide XP scoring function, are assigned a substantial amount of additional neutral-neutral hydrogen bond energy as compared to ordinary hydrogen bonds. The total neutral-neutral hydrogen bond energy is more than 5 kcal/mole. The second (FIG. 2) is the PDB complex 1d3d which is a complex between a ligand (shown in the Figure) and the protein thrombin. This complex has very low neutral-neutral hydrogen bond energy, less than 0.5 kcal/mole.

When docked and scored by Glide XP, the complex 1aq1 is accurately docked but the scoring is significantly overbound as compared to experiment. The strain energy induced by the buried rings can explain this overbinding (by ~6 kcal/mole), and appropriate parameterization can bring the predicted binding affinity of 1aq1 into good agreement with experiment. For the complex 1d3d, Glide XP again does an excellent job of docking. However, the predicted binding affinity from Glide XP is in good agreement with experiment (within 1.0 kcal/mole) without any ring-induced strain energy term. If a ring induced strain energy were to be introduced on a scale comparable to that required for 1aq1, the agreement of the predicted binding affinity of 1d3d with experiment would become significantly worse, with errors of ~3-5 kcal/mole.

A simple solution to the above dilemma is to assume that ring strain corrections can be imposed only to the extent that there is neutral-neutral hydrogen bond energy which can be diminished by the hypothesized strain effects. The mechanism for imposing this condition, a simple cap on the ring strain energy computed from the neutral-neutral hydrogen bonding total energy, is discussed further below.

(4) We assume that surface structures do not implicate the phenomena described above; that is, their lipophilic pair score is appropriate (they are after all shielding one face of the ring, and a similar sized portion of the protein, from water), and that they do not induce strain energy which disrupts hydrogen bonds (since the lack of enclosure permits inexpensive adjustment of the ring to accommodate to the protein surface, and visa versa). Thus, no corrections are made for structures assigned to this category.

To assemble the final scoring function, one additional type of term is added. The model for strain energy described above addresses generic strain induced by inserting a bulky, rigid structure into an enclosed pocket. However, there are also specific protein reorganizations required to enable a particular type of ligand to bind to a particular receptor. Examples include opening of the allosteric pocket in HIV-RT to accommodate NNRTI inhibitors, movement of the a phenyl ring in CDK2 to allow hydrogen bonding in the hinge region, and movement of the activation loop in p38 map kinase to enable binding of DFG-out inhibitors. In general, the reorganizational cost is clearly receptor-specific; however, one can expect a "core reorganization" free energy penalty in other cases as well, which is not only receptor specific but is specific to a class of ligands binding to the receptor. In principle one could calculate such reorganization terms from atomistic simulation. Alternatively, one can also treat these core reorganization terms as adjustable parameters specific to the receptor and ligand class (where the ligand class is defined by the type of conformation the ligand induces in the receptor), to be determined empirically or by another method. We define the core reorganization energy for a given ligand and receptor, however computed, as ECR.

If all of the receptor-ligand complexes for a given receptor exhibit the same "core" binding mode, then the core reorganization energy has no effect on relative binding free energies (as it is identical for each ligand) and hence has no effect on rank ordering. On the other hand, if one wants to compare ligands with different core binding modes (e.g., DFG-in and DFG-out inhibitors for p38 map kinase), one assigns core reorganization values to the different loop configurations. Such assignments can be made by fitting to a few experimental data points; alternatively, one could estimate the relative values of the core reorganization from related receptors in an available data set, for example the PDB. For example, we use the same core reorganization model when a positively charged group is placed in the S1 pocket of both thrombin and factor Xa, whereas the "reverse" binders in both systems have a different parameter. The requirement to supply a core reorganization model means that the scoring function we describe herein is not strictly a "global" model; some minimal amount of "local", receptor, and ligand class-specific input is needed, at least if the system under study has multiple core binding modes. However, this represents a small number of parameters, at which one can at least empirically estimate (if necessary) based on the structures associated with the core binding motifs.

Following is a step by step protocol for calculating the components of the ligand-receptor binding affinity which can be derived from the ring classification methodology described above:

(1) Each ring structure is classified as discussed above. The detailed mathematics of the classification scheme is presented in the Appendix.

(2) The lipophilic atom-atom pair contribution for solvent exposed ring structures, denoted ESOR, represents a reduction (by the value ESOR) in the ligand-receptor binding affinity, assuming that a favorable term of this type has been calculated in a different component of the scoring function. Alternatively, one can from the beginning eliminate any contribution to the hydrophobic interaction energy of solvent exposed ring structures.

(3) A non-fused (single) ring structure is assigned a "ring structure score" of 1 if it is buried, and is assigned a score of 0 otherwise. For fused structures, the buried sub-structure with the largest enclosure score is assigned a ring structure score of 1; other ring sub-structures that are classified as buried are assigned a value of 0.5; surface or solvent exposed substructures are assigned a value of zero. The ring scores of all rings are then added together to produce a total ring score R for the molecule.

(4) The ring score R is adjusted if necessary to take into account ring structure participation in the core reorganization energy ECR. In our current best practice implementation, if a ring structure is specifically involved in core reorganization, the contribution of that ring to R is subtracted from R. For example, if a single, buried ring is involved in core reorganization, the value of R is revised to R−1.

(5) The total neutral-neutral hydrogen bond energy EHB is computed, including contributions from "special" neutral-neutral hydrogen bonding terms if the Glide XP scoring function is being used to assign the neutral-neutral hydrogen bond energy. Special neutral-neutral hydrogen bonding terms in the Glide XP scoring function are defined in U.S. patent application Ser. No. 11/373,684 (US 2007/061118).

(6) The ligand is classified as belonging to a particular binding motif and assigned a core reorganization energy EC. As indicated above in (4), if a ring structure on the ligand is explicitly involved in core binding motif (as in CDK2), then this structure is ultimately not included (e.g., its contribution is subtracted from) the structure score R to avoid double counting.

(7) The total ring strain energy ER is computed as ER=R*A kcal/mole. The parameter A can be determined empirically or by trial-and-error. In some implementations, $0.5$ kcal/mole$\leq A \leq 2.5$ kcal/mole.

(8) The maximum amount of hydrogen bond energy that can be affected by ring strain of the ligand, the hydrogen bond capping energy HBC, is estimated as HBC=(EHB−B))*C. The parameter B can be determined empirically or by trial-and-error. This parameter reflects the phenomenon that strain becomes important when multiple hydrogen bonds have to be maintained in good geometrical positions. In some implementations, $0.5$ kcal/mole$\leq B \leq 2$ kcal/mole. The parameter C is a scale factor that measures the maximum fraction of the remaining hydrogen bond energy that can be lost due to strain. This parameter can also be determined empirically or by trial-and-error. In some implementations, $0.5 \leq C \leq 1.0$ (9) If ER is greater than HBC, ER is replaced by HBC. Otherwise, ER remains as computed.

(10) The ligand is assigned a core reorganization energy ECR based on the receptor and the ligand binding mode, as is discussed above.

(11) The total contribution to binding affinity due to solvent exposure, core reorganization, and strain energy, as defined by the above protocol, is then ER+ECR−ESOR.

(12) The above terms represent only a part of the calculated total ligand binding affinity. To compute the total ligand binding affinity, the terms in (11) are added to a scoring function representing these other terms, such as the Glide XP scoring function. If the value of the binding affinity defined by this other scoring function is E0, the total binding affinity after the contribution from solvent exposure, core reorganization, and strain energy is then E0+ER+ECR−ESOR.

As an initial demonstration of the utility of the invention, we have applied our current best practice protocol (as described in 1-12 above and in the Appendix) to 7 receptors from the PDB. For the PDB receptors, we performed self-docking for all of the relevant protein-ligand complexes derived from that receptor (except for the case of ns5b, where we utilized only ligands docking into a specific allosteric site of the receptor), carried out self-docking with the Glide XP methodology, and eliminated complexes where the ligand was substantially misdocked by Glide XP (corresponding overall to less than 5% of all complexes). For the remaining complexes, we modified the Glide XP score as defined by (12) above, using the parameters A=1.5 kcal/mole, B=1.0 kcal/mole, and C=0.75, which constitute our current best practice values, and core reorganization parameters for each receptor as appropriate (no more than two such parameters were used for any receptor). The results of these calculations of binding affinity of the complex are compared with experimental data (for all complexes for which it was available) in FIGS. 4-10. FIGS. 4-10 plot experimental binding affinity versus calculated binding affinity, but also present the correlation coefficient $R^{}2$ for the plot and the mean absolute deviation (MAD) of the plot. The range of MAD values (0.75-1.24 kcal/mole) and $R^{}2$ values (0.47-0.62), demonstrate a high degree of consistency and represent significant practical utility in discriminating compounds with various levels of activity. Considering that the new model is a global scoring function, with 1-2 receptor specific parameters (only the second of which affects the MAD and $R^{**}2$), we believe that a significant advance has been achieved as compared to alternative global scoring functions in the literature.

What is claimed is:

1. A computer-implemented method of quantifying binding affinity between a ligand and a receptor molecule, the method comprising:
   receiving by one or more computers, data representing a ligand molecule,
   receiving by one or more computers, data representing a receptor molecule,
   using the data representing the ligand molecule and the data representing the receptor molecule in computer analysis to identify ring structure within the ligand, the ring structure being an entire ring or a fused ring;
   using the data representative of the identified ligand ring structure to designate a first ring face and a second ring face opposite to the first ring face, and classifying the ring structure by:
   a) determining proximity of receptor atoms to atoms on the first face of the ligand ring; and
   b) determining proximity of receptor atoms to atoms on the second face of the ligand ring;
   c) determining solvation of the first face of the ligand ring and solvation of the second face of the ligand ring;
   classifying the identified ligand ring structure as buried, solvent exposed or having a single face exposed to solvent based on receptor atom proximity to and solvation of the first ring face and receptor atom proximity to and solvation of the second ring face;
   quantifying the binding affinity between the ligand and the receptor molecule based at least in part on the classification of the ring structure; and
   displaying, via computer, information related to the classification of the ring structure.

2. The method of claim 1, in which quantifying the binding affinity includes a step that scores hydrophobic interactions between one or more ligand atoms and one or more receptor atoms by awarding a bonus for the presence of hydrophobic enclosure of one or more atoms of said ligand by the receptor molecule, said bonus being indicative of enhanced binding affinity between said ligand and said receptor molecule.

3. The method of claim 1 comprising calculating an initial binding affinity and then adjusting the initial binding affinity based on the classification of the ring structure as buried, solvent exposed or solvent exposed on one face.

4. The method of claim 1, in which the classification of a ring structure as buried, solvent exposed, or solvent exposed on one surface, includes using a parameter substantially correlated with the number of close contacts on both sides of the ring structure or part thereof with the receptor molecule.

5. The method of claim 1 in which the number of close contacts at different distances between receptor atoms and the two ring faces are determined, an initial classification of the ring is made based on the numbers of these contacts, and this initial classification is then followed by calculation of a scoring function, said scoring function comprising identifying a first ring shell and a second ring shell, and calculating the number of water molecules in the first shell and in the second shell, or calculating the number of water molecules in the first and second shell combined.

6. The method of claim 5, wherein the scoring function enabling classification of the ring structure as buried, solvent exposed, or solvent exposed on one surface, includes using a parameter substantially correlated with the lipophilic-lipophilic pair score between the ring structure or part thereof and the receptor molecule.

7. The method of claim 5, in which the scoring function used to classify a ring structure as buried, solvent exposed, or solvent exposed on one surface, includes calculating the degree of enclosure of each atom of the ring structure by atoms of the receptor.

8. The method of claim 5, in which the scoring function used to classify a ring structure as buried, solvent exposed, or solvent exposed on one surface, includes using a parameter that is substantially correlated with the degree of enclosure of each atom of the ring structure by atoms of the receptor.

9. The method of claim 1 or claim 5, wherein the scoring function enabling classification of the ring structure as buried, solvent exposed, or solvent exposed on one surface, includes the use of a parameter corresponding to a hydrophobic interaction of the ring structure or part thereof with the receptor molecule.

10. The method of claim 9 in which the information displayed by computer includes a depiction of at least one of:
    the degree to which the ring structure is enclosed by atoms of the receptor molecule;
    water molecules surrounding the ring structure in a first shell or a second shell or both the first and the second shell of the ligand;
    a value of a lipophilic-lipophilic pair score of the ring structure; and
    a number of close contacts of a face of the ring structure with the receptor molecule.

11. The method of claim 1, in which solvent exposed ring structures in the ligand, if any, are substantially ignored in quantifying the component of the binding affinity between the ligand and the receptor molecules, other than to recognize hydrogen bonds and other parameters that are independent of the classification of ring structure.

12. The method of claim 1, in which hydrophobic contribution to binding affinity from ring structures classified as solvent exposed, if any, is substantially ignored in quantifying the component of the binding affinity.

13. The method of claim 1, in which a ring structure is classified as buried, and the method further comprises:
    identifying a quantity representative of a strain energy induced in the ligand-receptor complex by the buried ring structure, in which the quantification of the component of binding affinity is further based in part on strain energy.

14. The method of claim 13, further comprising
    identifying a quantity representative of a strain energy induced in the ligand-receptor complex by the aggregate of the ring structures identified as buried;
    identifying a quantity representative of a total neutral-neutral hydrogen bond energy; and
    quantifying the component of binding affinity between the ligand and the receptor molecule based at least in part on the quantity representative of the strain energy induced in the receptor by the aggregate of the buried ring structures, and on the quantity representative of the total neutral-neutral hydrogen bond energy.

15. The method of claim 14, in which quantifying the component of binding affinity further comprises identifying a hydrogen bond capping energy associated with the entire ligand, and the component of binding affinity is quantified based on a greater of the hydrogen bond capping energy and the quantity representative of the strain energy induced in the receptor by the aggregate of the identified structures.

16. The method of claim 14, further comprising:

identifying a binding motif of the receptor molecule with respect to the ligand;

identifying a reorganization energy of the receptor molecule based on the binding motif; and identifying a first ring structure as contributing to the reorganization energy, the quantity representative of strain energy being identified independently of the classification of the first ring structure.

17. The method of claim 13, in which the component of binding affinity attributable to strain is quantified using at least one of: molecular dynamics, molecule mechanics, conformational searching and minimization.

18. The method of claim 1, in which the information displayed by computer includes a depiction of solvent exposure, if any, of the ring structure.

19. The method of claim 1, in which the information displayed by computer includes a depiction of burial, if any, of the ring structure.

20. The method of claim 1, in which the information displayed by computer includes a depiction of at least one of:

the degree to which the ring structure is enclosed by atoms of the receptor molecule;

water molecules surrounding the ring structure in a first shell or a second shell or both the first and the second shell of the ligand;

a value of a lipophilic-lipophilic pair score of the ring structure; and a number of close contacts of a face of the ring structure with the receptor molecule.

21. The method of claim 1 further comprising, performing a test on a physical sample that includes the ligand and the receptor molecule, test components being selected based at least in part on the binding affinity between the ligand or part thereof and the receptor molecule, or on the component of such binding affinity.

* * * * *